United States Patent
Abend et al.

(10) Patent No.: US 7,066,888 B2
(45) Date of Patent: Jun. 27, 2006

(54) METHOD AND APPARATUS FOR DETERMINING AN ULTRASOUND FLUID FLOW CENTERLINE

(75) Inventors: Kenneth Abend, Huntingdon Valley, PA (US); Alan Stein, Cherry Hill, NJ (US)

(73) Assignee: Allez Physionix LTD, Seattle, WA (US)

( * ) Notice: Subject to any disclaimer, the term of this patent is extended or adjusted under 35 U.S.C. 154(b) by 0 days.

(21) Appl. No.: 10/976,729

(22) Filed: Oct. 29, 2004

(65) Prior Publication Data
US 2005/0124885 A1    Jun. 9, 2005

Related U.S. Application Data

(60) Provisional application No. 60/515,350, filed on Oct. 29, 2003.

(51) Int. Cl.
*A61B 8/14* (2006.01)

(52) U.S. Cl. .................................... 600/454

(58) Field of Classification Search ........ 600/437–472; 73/625, 626; 128/916; 367/7, 11, 130, 138
See application file for complete search history.

(56) References Cited

U.S. PATENT DOCUMENTS

| | | | |
|---|---|---|---|
| 5,148,810 A * | 9/1992 | Maslak et al. ............... | 600/447 |
| 5,261,408 A * | 11/1993 | Maslak et al. ............... | 600/447 |
| 5,278,757 A | 1/1994 | Hoctor et al. | |
| 5,291,892 A | 3/1994 | O'Donnell | |
| 5,406,163 A | 4/1995 | Carson et al. | |
| 5,409,010 A | 4/1995 | Beach et al. | |
| 5,460,180 A | 10/1995 | Klepper et al. | |
| 5,546,807 A | 8/1996 | Oxaal et al. | |
| 5,623,930 A * | 4/1997 | Wright et al. ............... | 600/456 |
| 5,701,898 A | 12/1997 | Adam et al. | |
| 5,722,412 A | 3/1998 | Pflugrath et al. | |
| 5,787,049 A | 7/1998 | Bates | |
| 5,808,962 A | 9/1998 | Steinberg et al. | |
| 5,817,024 A | 10/1998 | Ogle et al. | |
| 5,840,033 A | 11/1998 | Takeuchi | |
| 5,911,692 A | 6/1999 | Hussain et al. | |
| 5,922,962 A | 7/1999 | Ishrak et al. | |
| 5,928,151 A | 7/1999 | Hossack et al. | |
| 5,944,666 A | 8/1999 | Hossack et al. | |

(Continued)

OTHER PUBLICATIONS

C. Kasai, K. Namekawa, A. Koyano and R.Omoto, "Real-Time Two Dimensional Blood Imaging Using An Autocorrelation Technique", IEEE Transactions On Sonics and Ultrasonics, vol. SU-32, No. 3, pp. 458-464, May 1985.

(Continued)

*Primary Examiner*—Ali Imam (57) ABSTRACT

A method and associated apparatus are disclosed for determining the location of an effective center of fluid flow in a vessel using an ultrasound apparatus. Ultrasound energy is propagated along an axis of propagation and projects upon the vessel. A Doppler-shifted signal reflected from the fluid in the vessel is received and a set of quantities expressed as a density is derived from the Doppler shifted signal for each of a set of coordinates, the density being a function of the Doppler shift in frequency associated with each of the coordinates. One of a mean, mode or median is calculated for each of the dimensions of the set of coordinates in conjunction with the density associated therewith. This calculation is repeated throughout the field of view of the vessel to define a centerline.

29 Claims, 7 Drawing Sheets

U.S. PATENT DOCUMENTS

| | | |
|---|---|---|
| 5,971,927 A | 10/1999 | Mine |
| 6,066,096 A | 5/2000 | Smith et al. |
| 6,080,107 A | 6/2000 | Poland |
| 6,135,971 A | 10/2000 | Hutchinson et al. |
| 6,148,095 A * | 11/2000 | Prause et al. ............... 382/131 |
| 6,186,949 B1 | 2/2001 | Hatfield et al. |
| 6,228,031 B1 | 5/2001 | Hwang et al. |
| 6,238,346 B1 | 5/2001 | Mason |
| 6,524,253 B1 | 2/2003 | Abend |
| 6,682,483 B1 | 1/2004 | Abend |
| 6,682,488 B1 | 1/2004 | Abend |
| 2002/0151790 A1 | 10/2002 | Abend |
| 2004/0019278 A1 | 1/2004 | Abend |
| 2004/0254468 A1 | 12/2004 | Herzog et al. |
| 2004/0267127 A1 | 12/2004 | Abend et al. |
| 2005/0004461 A1 | 1/2005 | Abend |
| 2005/0004464 A1 | 1/2005 | Miller |
| 2005/0124885 A1 | 6/2005 | Abend et al. |

OTHER PUBLICATIONS

K. Ferrara and G. De Angelis, "Color Flow Mapping", Ultrasound in Medicine and Biology, vol. 23, No. 2, pp. 321-345, Mar. 1997.

T. Buck, et al., "Flow Quantification in Valvular Heart Disease Based on the Integral of Backscattered Acousitc Power Using Doppler Ultrasound", Proc. IEEE, vol. 88, No. 3, pp. 307-330, Mar. 2000.

* cited by examiner

METHOD AND APPARATUS FOR DETERMINING AN ULTRASOUND FLUID FLOW CENTERLINE

CROSS-REFERENCE TO RELATED APPLICATION

This application claims the benefit of U.S. Provisional Application Ser. No. 60/515,350 filed Oct. 29, 2003, the disclosure of which is incorporated herein by reference in its entirety.

FIELD OF THE INVENTION

The present invention relates to ultrasound data processing, and more particularly, to finding the attributes of fluid flow in a living body, such as ascertaining the speed, direction, and volume of a fluid flow in a vessel using ultrasound.

BACKGROUND OF THE INVENTION

Several techniques exist for locating an object using wave-propagation. In the fields of sonar, radar, ultrasound, and telecommunications, transmitting/receiving elements are placed in an array. Some or all of the elements of the array emit pulses of electromagnetic radiation or sound toward a target, and reflections of the wave pattern from the target are received at some or all of the elements. To receive the maximum amplitude (strongest signal) possible, the received signals from all the elements are focused into a beam.

Figure 1:
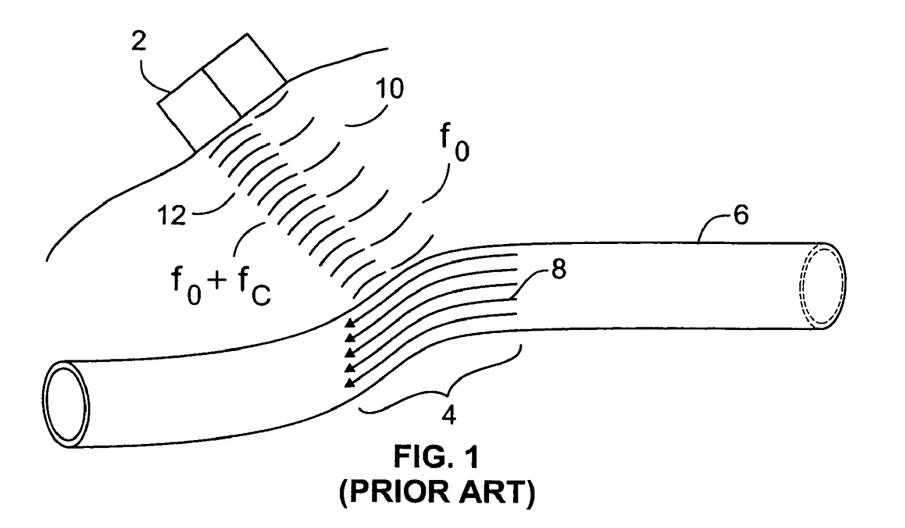
FIG. 1 is a diagrammatic view of an ultrasound probe transmitting ultrasound waves to and receiving reflected waves from a blood vessel as is known in the prior art.

To determine blood flow velocity from a beam, techniques from Doppler radar may be adapted for use in ultrasound imaging. With reference to FIG. 1, acoustical energy from an ultrasound probe 2 is aimed at a region 4 of a blood vessel 6 through which blood 8 is flowing with a certain velocity. Wavefronts 10 of acoustical energy impinge on the region 4 with a frequency $f_0$. The wavefronts 12 returning from region 4 of the blood vessel 6 are shifted in frequency to a value of $f_0+f_c$, the change in frequency $f_c$ being proportional to double the velocity of the flow of blood 8. The frequency $f_0$ of the carrier wavefronts 10 is on the order of megahertz, while the frequency of the Doppler shift $f_c$ is on the order of kilohertz. The greater the velocity of the blood 8 the greater the frequency shift $f_c$. The frequency shift $f_c$ and the blood flow velocity are related to the speed of sound in soft tissue, c, which is nearly a constant of about 1540 meters/second. Known ultrasound equipment may be used to measure the radial component of blood flow, i.e., the component parallel to the direction of sonic propagation, rather than the true velocity v.

Known ultrasound imaging equipment displays the radial component of blood flow (or the power associated therewith) by translation into a color scale. Given this colorized display, the direction of flow is estimated by a skilled sonographer and input into a 2-D display in order to enable the approximate calculation of actual velocity (as opposed to its radial component) at one point in the vessel.

A drawback of this manual approach is that even for a skilled sonographer, the resultant true velocity is only approximate. Another drawback is that the sonographer needs to use both hands and eyes to obtain a single measurement. The sonographer manipulates an ultrasound probe with one hand and manipulates a joy stick or track ball with the other hand, all while observing the ultrasound image on a screen. The sonographer uses the joy stick or track ball to "draw" a line segment parallel to the blood flow on the screen and then have the ultrasound equipment compute an approximate "true" velocity from the measured radial velocity. The computation is made by utilizing the relationship between the true velocity at a point in a blood vessel to the radial component of velocity by s=v cos θ where s is the magnitude of the true velocity and θ is the angle (2-dimensional for 2-D ultrasound imaging or 3-dimensional for 3-D or 4-D ultrasound imaging) between the radial velocity measured by the probe and the actual direction of flow, which is approximated by the line drawn on the screen by the sonographer.

It is difficult to get a good approximation of the angle θ using this two hand manual approach. Traditionally, peak systolic blood velocity at one point has been obtained with this method. However, it is difficult, if not impossible, to obtain other desirable parameters such as volume flow (the amount of blood flowing through a given cross-sectional area of the blood vessel) and lumen area (the total area of a cross section perpendicular to the blood vessel at a given point) with the use of this method. Nor can true velocity be obtained at more than one point, such as the full field of view of the blood vessel 6. To calculate values accurately, it is necessary to find the true vector velocity of blood flow, including magnitude and direction, over the entire field of view.

SUMMARY OF THE INVENTION

The disadvantages and limitations of prior art ultrasound apparatus and methods are overcome by the present invention which includes, a method for determining the location of an effective center of a fluid flow in a vessel using an ultrasound apparatus with a transducer array for propagating and receiving ultrasound energy. Ultrasound energy is propagated along an axis of propagation Z, which can be described by a spacial coordinate system (x, y, z) in which the dimension z is in the same direction as the axis of propagation Z. The ultrasound energy projects upon the vessel defining a set of coordinates in the spacial coordinate system where the ultrasound energy impinges upon fluid in the vessel at a given value of the dimension y. A Doppler-shifted signal reflected from the fluid in the vessel at a plurality of the set of coordinates is received and a set of quantities expressed as a density a is derived from the Doppler shifted signal for each of the set of coordinates, the density being a function of the Doppler shift in frequency associated with each of the coordinates, the density being indicative of the movement of the fluid. One of a mean, mode or median is calculated of each of the dimensions of the set of coordinates in conjunction with the density associated therewith.

The steps above are repeated after changing the set of coordinates to a second set of coordinates to determine another center in the fluid flow at a different point along the length of the vessel and then determining a vector v which connects the two centers and indicates the approximate direction of flow and the approximate centerline. In a similar manner, a plurality of center points and vectors can be determined using the method just described to ascertain a centerline of the vessel over an entire field of view.

Further features and advantages of the invention are described in the following detailed description of an exemplary embodiment of the invention, by way of example with reference to the accompanying drawings.

BRIEF DESCRIPTION OF THE DRAWINGS

For a more complete understanding of the present invention, reference is made to the following detailed description of an exemplary embodiment considered in conjunction with the accompanying drawings, in which.

DETAILED DESCRIPTION OF THE INVENTION

Figure 2:
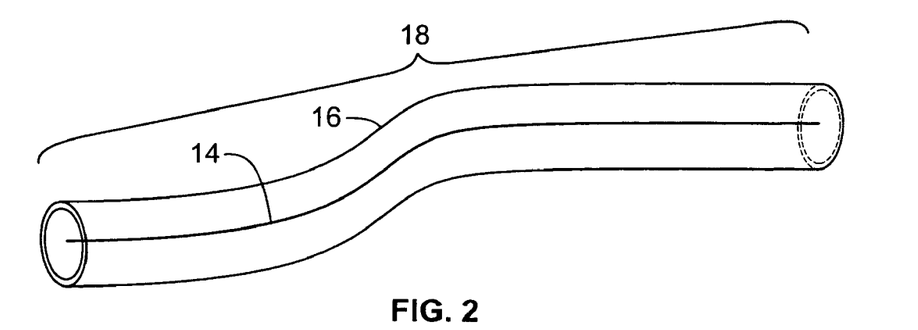
FIG. 2 is a diagrammatic view of a centerline of a vessel determined in accordance with an exemplary embodiment of the present invention.
Figure 3:
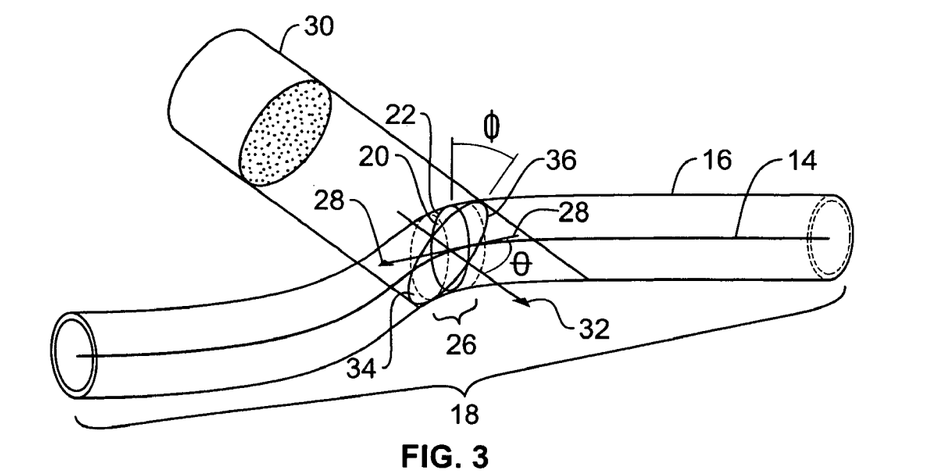
FIG. 3 is a diagrammatic view of the vessel of FIG. 2, showing a first surface defined by the intersection of the wavefronts of an ultrasound probe with the vessel and a second surface defined by the cross-sectional area of the vessel perpendicular to the centerline of the vessel at a line intersecting the first surface.

With reference to FIGS. 2 and 3, a centerline 14 is drawn through a vessel 16 (e.g. a blood vessel) within the body of a living being (e.g. a human) within the field of view 18 of an ultrasound probe (not shown). The centerline 14 is defined as a plurality of statistical "centers" of the vessel 16 throughout the field of view 18. The centerline 14 is derived from measured ultrasound parameters such as 4-D Power Doppler or 4-D color flow data. It can be, for instance, the mean (average), median (central value), or mode (location of maximum) of samples of ultrasound measurements taken over successive cross-sections of areas 20 along the vessel 16. The mean of a dimension x representing the x dimension in the coordinate system of the frame of reference of the ultrasound probe using a(x) as a density of some desirable ultrasound parameter is $\int x a(x) dx$, provided that a(x) is normalized so that it integrates to unity. The median is the value $x_0$ such that $$\int_{-\infty}^{x_0} a(x)\, dx = \int_{x_0}^{\infty} a(x)\, dx,$$

and the mode is the value $x_p$ for which $$\max_x \{a(x)\} = a(x_p).$$

Figure 4:
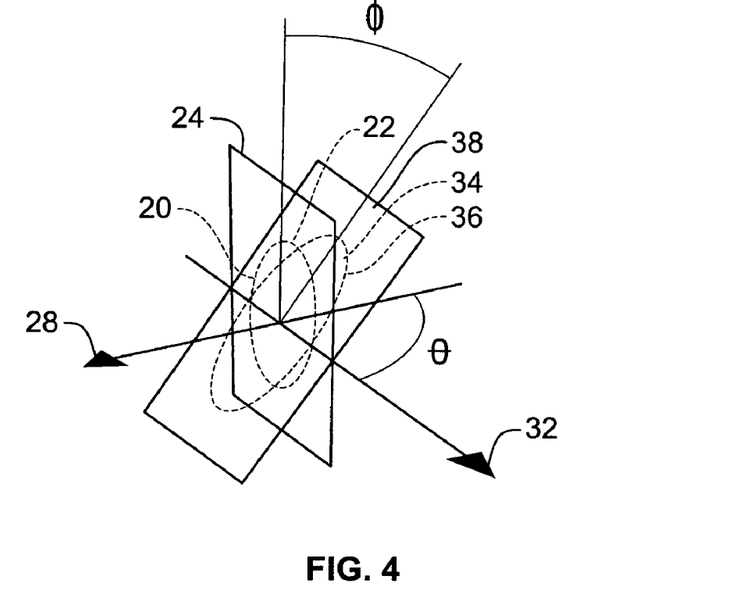
FIG. 4 is a perspective view of the planes associated with the first and second surfaces depicted in FIG. 3, along with vectors parallel to the centerline and parallel to the direction of propagation of the ultrasound wave and the angles between the respective vectors and planes.

Now referring to FIGS. 3 and 4, the cross-section of area 20 forms a circle 22 in a plane 24 for 3-D or 4-D imaging if the vessel 16 can be modeled in a small region as a right-circular cylinder 26 and is perpendicular to the direction of fluid flow 28 through the vessel 16. In contrast, a Doppler ultrasound probe 30 propagates ultrasound waves in a direction 32 through the vessel 16. That ultrasound energy can be thought of as projecting onto an area 34 of the vessel 16 which forms an ellipse 36 in a plane 38 which contains the direction 32 of wave propagation. The direction of the centerline 14 is the same as the direction of fluid flow 28, which is taken to be the average direction of all flow of fluid (e.g. blood) in any cross-section plane 24 through the centerline 14. If fluid flow is measured as an average velocity of fluid flowing past the area 20 by the ultrasound equipment, and if that velocity were not along the centerline 14, fluid would have to leak out of the vessel 16. In any plane 22, 38 drawn through the vessel 16, the components of velocity perpendicular to the centerline 14 are assumed to average to zero. If not, there would be a net flow of fluid through the vessel walls. Since the average velocity direction is along the centerline 14 and only the component of velocity in the direction of wave propagation 32 of the ultrasound probe emitted energy can be measured, then it can be assumed, in the case of blood as the fluid, that all blood cells are moving parallel to the centerline 14. It does not matter if this is not correct for every blood cell; it will be correct on average. The net flow or flux (integrated over the cross-sectional area 20, 34) will be in the direction of the centerline 14.

The direction of wave propagation 32 of the ultrasound probe emitted energy forms an angle θ with the direction of fluid flow 28. Similarly, the plane 38 forms an angle φ with plane 24. Since Doppler cannot measure true velocity s, but only its radial component, s cos θ, it is necessary to find the direction of fluid flow 34 and thus the direction of the centerline 14 relative to the direction 32 of wave propagation in order to correct for the angle θ. Likewise to find the proper orientation of cross-section of area 20 from the orientation of area 34 in order to find, say, the lumen area, then it is necessary to correct for the angle φ.

Figure 5:
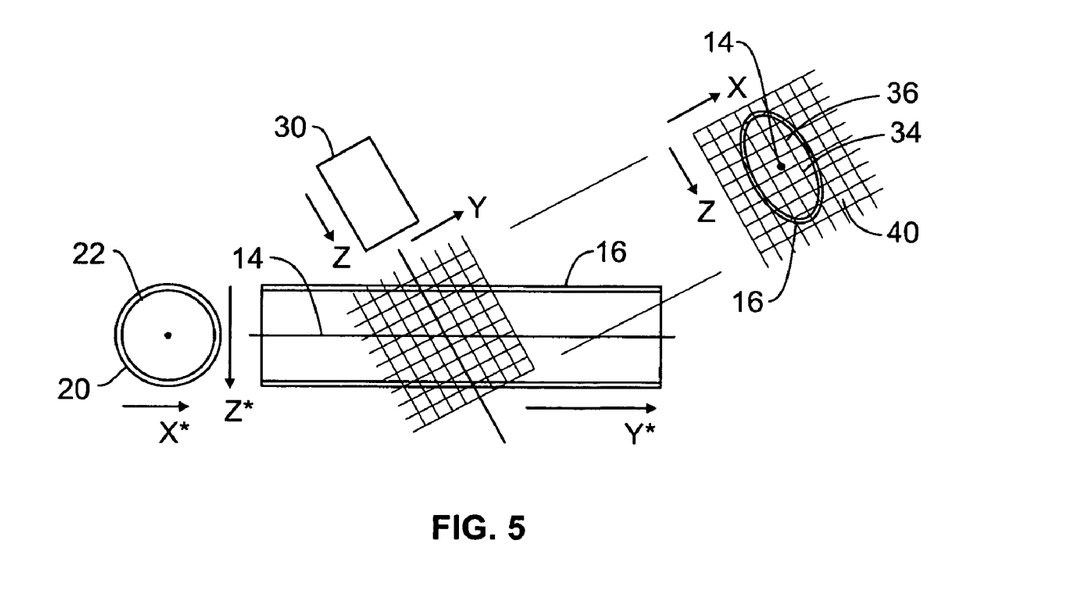
FIG. 5 is a schematic view of two rectangular coordinate systems imposed on a vessel and its associated centerline in three-on-two dimensions looking into the lumen of the vessel.
Figure 6:
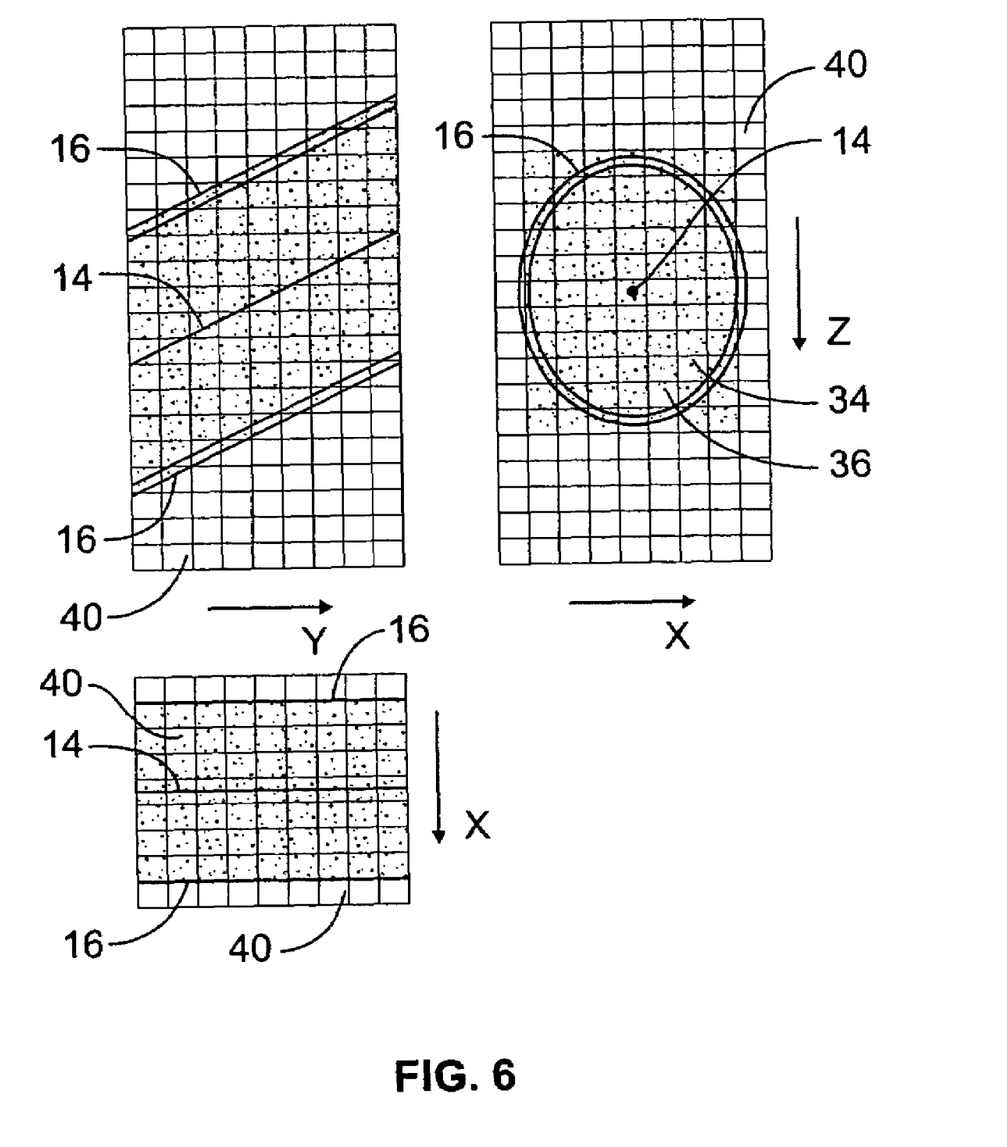
FIG. 6 is a schematic view of the projections of the vessel and centerline onto the coordinate planes of FIG. 5.

With reference to FIGS. 5 and 6, to correct for θ and φ, it is necessary to impose a coordinate system of the reference frame of the ultrasound probe 30 onto the vessel 16. The vessel 16, in three dimensions is referenced, for example, by a rectangular coordinate system with dimensions x*, y*, z*, where x* and z* are the dimensions of the cross-section plane 24 perpendicular to the centerline 14, and y* is measured parallel to the centerline 14. The dimensions x, y, and z are the axes with reference to the ultrasound probe 30 where z is in the direction of ultrasound propagation from the probe 30, the x-y plane at z=0 is the plane of the transducers (not shown) of the probe 30, and the x-z plane at a fixed value of y cuts through the vessel 16 under examination, i.e., the plane 38 through the vessel 16 (to create the ellipse 36 if the vessel 16 is a circular cylinder).

If the plane 38 is divided into a large number of rectangular regions 40, then each region 40 represents a three dimensional pixel known as a voxel. If the centerline 14 is defined with reference to a mean position of x and z dimensions at a fixed y on the plane 38, then a point on the centerline 14 is given by the mean of the center, i.e. a point with dimensions x(y), y, z(y) such that $$\bar{x}(y) = \frac{\sum_n x_n a_n}{\sum_n a_n} = \frac{\sum_{x,z} x a(x, y, z)}{\sum_{x,z} a(x, y, z)} \quad (1)$$

$$\bar{z}(y) = \frac{\sum_n z_n a_n}{\sum_n a_n} = \frac{\sum_{x,z} z a(x, y, z)}{\sum_{x,z} a(x, y, z)} \quad (2)$$

at a given time t where n is the $n^{th}$ voxel within the ellipse 36.

The centerline 14 is calculated from the density variable a(x, y, z) which is based on 2-D, 3-D, or 4-D Power Doppler or Color Doppler image data (after a Wall filter). The Power Doppler or Color Doppler densities a(x, y, z) are derived with the use of the method disclosed in International Patent Publication No. WO 00/72756 (i.e., international Patent Application No. PCT/US00/14691) and U.S. Pat. No. 6,524,253 B1, the disclosures of which are incorporated herein by reference in their entirety. With reference to page 34, lines 18–21, of International Patent Publication No. WO 00/72756, a generalized Doppler spectrum can be denoted by a 5-dimensional data set $A_1$(r, a, e, f, t) which is the real-time signal return amplitude of what is being measured (to obtain blood flow velocity), where r=depth (or range), a=azimuth, e=elevation, f=Doppler frequency, and t=time. Such a data set can be readily converted to rectangular coordinates, where it becomes $A_2$(x, y, z, f, t) or $A_3$(x, y, z, v, t) where v is the radial velocity, the component of velocity of fluid flow in the direction 32, and v is related to Doppler frequency by the relation $$v = \frac{c}{2f_0} f,$$

where c and $f_0$ are the sonic propagation speed and frequency, respectively. A still more interesting 5-D data set would be $A_4$(x, y, z, s, t) where s is the fluid speed (e.g. blood speed), i.e., the signed magnitude of the true total vector velocity of fluid flow where v=s cos θ and θ is the angle described above for FIGS. 3 and 4.

A 4-D Doppler ultrasound machine as described in International Patent Publication No. WO 00/72756 and U.S. Pat. No. 6,524,253 B1 will produce three different 4-D data sets corresponding to the three common vascular imaging modes:

$$B(x, y, z, t) = A_2(x, y, z, 0, t) \quad \text{"4-D B-mode data"} \quad (3)$$

$$p(x, y, z, t) = \int_{f > f_0} |A_2(x, y, z, f, t)|^2 \, df \quad (4)$$

"4-D Power Doppler"

$$v(x, y, z, t) \quad \text{"4-D Color Doppler" or "4-D Color Flow."} \quad (5)$$

Figure 7:
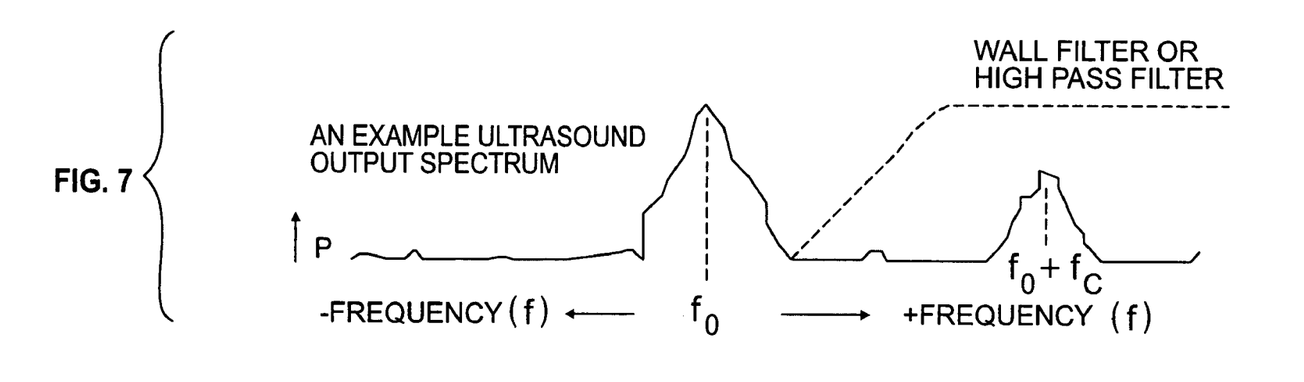
FIG. 7 is a frequency spectrum of the Doppler output power of the received signal vs. frequency both before and after a Wall filter.
Figure 8:
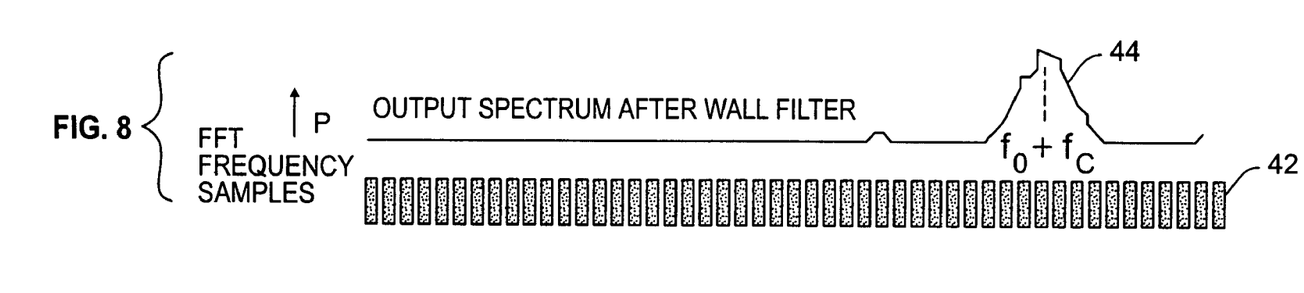
FIG. 8 is a frequency spectrum of the Doppler output power of the received signal vs. frequency after a Wall filter along with a graph depicting FFT sampling in the frequency range of the Doppler output power.

With reference to FIGS. 7, as is customary in Modern Doppler ultrasound, p plotted vs. frequency in FIG. 7, which has a peak surrounding the carrier frequency $f_0$ and another peak around $f_0+f_c$ where $f_c$ is the shift in frequency due to the Doppler effect. When passed through a Wall (high pass) filter (the dotted line in FIG. 7), the resulting plot of p vs. frequency is shown in FIG. 8, which is the density to be obtained (usually after first maximizing p (or v) with respect to t—a process called "peak hold"). The centerline 14 is the mean, mode, or median of x (or y) and z as a function of y (or x) using p as a density. For the case of a point on the centerline 14 given by the mean of the center, i.e. a point with dimensions x(y), y, z(y) based on density p, values of the dimensions x and z are thus:

$$\bar{x}(y) = \frac{\sum_n x_n p_n}{\sum_n p_n} = \frac{\sum_{x,z} x p(x, y, z)}{\sum_{x,z} p(x, y, z)} \quad (6)$$

$$\bar{z}(y) = \frac{\sum_n z_n p_n}{\sum_n p_n} = \frac{\sum_{x,z} z p(x, y, z)}{\sum_{x,z} p(x, y, z)} \quad (7)$$

The quantity v is the mean radial velocity of fluid flow corresponding to the measured amplitude $A_3$ as already discussed above, which is obtained using the autocorrelation function described in "Real-Time Two-Dimensional Blood Flow Imaging Using an Autocorrelation Technique," C. Kasai, K. Nemakawa, A. Koyano, and R. Omoto, *IEEE Transactions on Sonics and Ultrasonics*, vol. SU-32, no. 3, pp. 458–463, May 1985, which is incorporated herein by reference in its entirety. The centerline 14 for v is the mean, mode, or median of x(or y) and z as a function of y (or x) using v as a density. For the case of a point on the centerline 14 given by the mean of the center, i.e. a point with dimensions x(y), y, z(y) based on density v, values of the dimensions x and z are thus:

$$\bar{x}(y) = \frac{\sum_n x_n v_n}{\sum_n v_n} = \frac{\sum_{x,z} x v(x, y, z)}{\sum_{x,z} v(x, y, z)} \quad (8)$$

$$\bar{z}(y) = \frac{\sum_n z_n v_n}{\sum_n v_n} = \frac{\sum_{x,z} z v(x, y, z)}{\sum_{x,z} v(x, y, z)} \quad (9)$$

Since v is merely the radial component of velocity, it is desirable to calculate $$s(x,y,z,t) \text{ "4-D True Velocity Flow"} \tag{10}$$

s is the magnitude of the vector v, the vector of true velocity in the direction of fluid flow 28 at the centerline 14. Let n represent a voxel number (the $n^{th}$ voxel in or on the ellipse 36). The measured mean Doppler frequency, $f_n$, at each voxel is proportional to $v=v_z$, the z component of the mean velocity, $v_n$, in that resolution cell. The flow center can be defined as the locus of centers of the ellipses as y varies (i.e., along the centerline 14).

To derive v and s from $v_n$ which is itself derived from $f_n$ using the autocorrelation method mentioned above, let us obtain the complex output of the Wall filter in each bin n, or $u_{nj}$. If $N_s$ ultrasound pulses are used ($N_s \leq 32$) with an $N_f$-tap Wall filter ($N_f \leq 11$), there will be $J=N_s-N_f+1$ values of j. Ignoring the voxel identifier, n (to simplify notation), let the autocorrelation vector $u_1=(u_1, u_2 \ldots u_{J-1})^t$ and let $u_2=(u_2, u_3 \ldots u_J)^t$ where $u_1$ is autocorrelated with $u_2$, $u_2$ is autocorrelated with $U_3$, etc. Let $F=u_1*u_2$ (the complex inner product, where * is the conjugate transpose), then $$f_n=(PRF/2\pi)\text{angle}(F) \tag{11}$$

and $$\text{angle}(F)=a\tan_2[Im(F)/Re(F)] \tag{12}$$

where PRF is the ultrasound pulse repetition frequency. Put another way, the quantity F is the autocorrelation function of the complex wall filter output at a lag of one. The 3-D orientation of the centerline 14 and hence the direction of the vector velocity v can be computed, for example, by using two consecutive values of y, forming the vector $$v=(v_x, v_y, v_z) \propto (\bar{x}(y_2)-\bar{x}(y_1), y_2-y_1, \bar{z}(y_2)-\bar{z}(y_1)) \tag{13}$$

which can be transformed into a unit vector by dividing by the square root of the sum of the squares of the three coordinate differences. The magnitude of the velocity is then obtained by dividing the measured radial velocity by the cosine of the 3-Doppler angle $\theta$ to determine the speed $s_n$ at each voxel. Thus if $f_n(x,y,z)$ is the Doppler frequency calculated above and $s_n=s(x,y,z)$ is the blood speed, then $$s_n(x,y,z) = \frac{c}{2f_0} \frac{\sqrt{(x-a)^2+(y-b)^2+z^2}}{(x-a)v_x+(y-b)v_y+zv_z} f_n(x,y,z) \tag{14}$$

where (a, b, 0) is the center of the sub-array of the ultrasound probe currently active to observe the point (x, y, z). The constant c is the speed of sound in soft tissue, about 1540 meters/second or mm/millisecond, and $f_0$ is the center frequency or carrier frequency of the ultrasound energy being used. A more convenient way to express this formula is to choose two points on the vessel centerline 14, near where $f_n$ was measured, and let the coordinates of one with respect to the other be $(x_c, y_c, z_c)$. The true speed $s_n$ of a voxel is then given by $$s_n = \frac{c}{2f_0} \frac{f_n}{\cos\theta} = \frac{cf_n}{2f_0} \frac{\sqrt{x_c^2+y_c^2+z_c^2}}{z_c} \tag{15}$$

Figure 10:
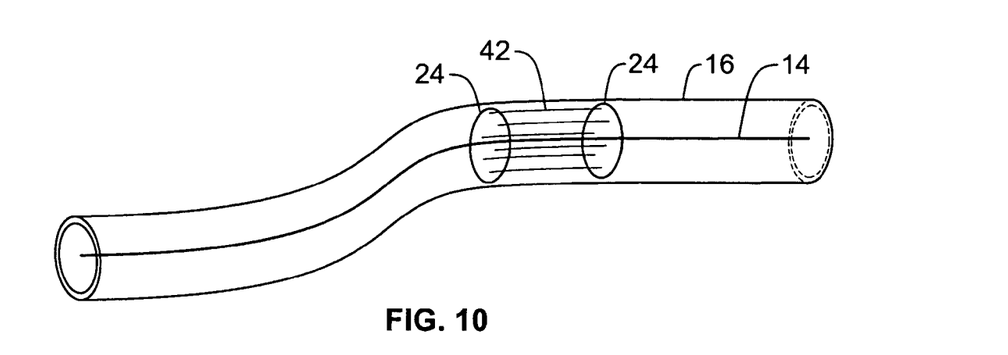
FIG. 10 is a diagrammatic view of the vessel of FIG. 2 with a superimposed diagrammatic representation of volume flow within the vessel in the vicinity of the centerline.
Figure 11:
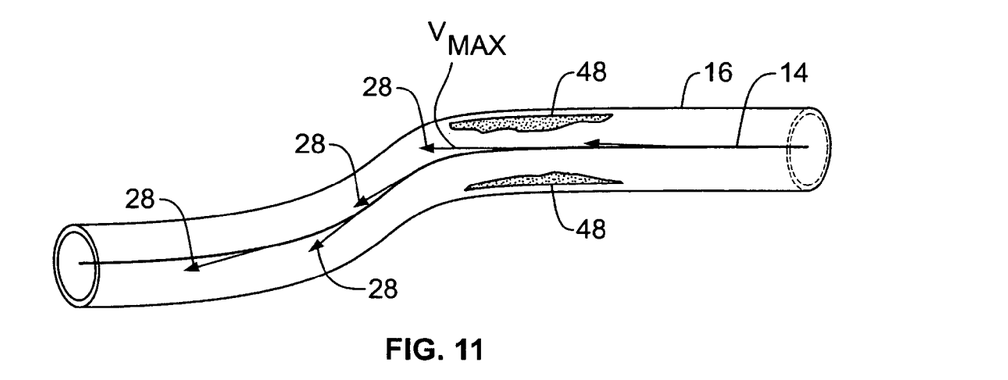
FIG. 11 is a diagrammatic view of a blood vessel with a stenosis.
Figure 12:
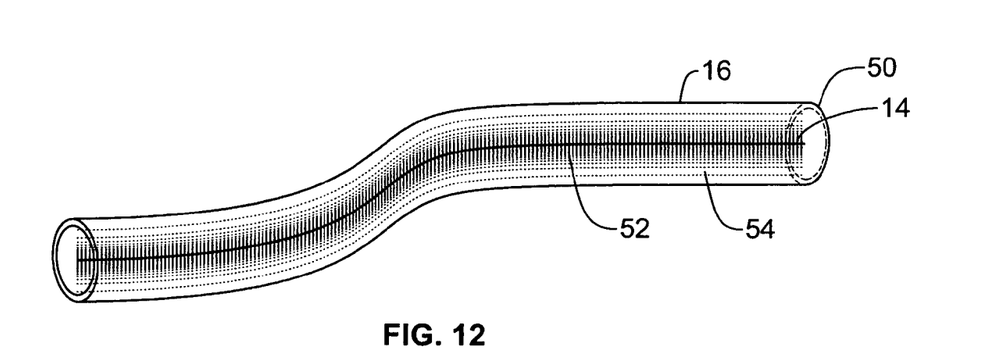
FIG. 12 is a diagrammatic view of the vessel of FIG. 2 with a superimposed diagrammatic representation of a measure of "translucency" within the vessel.
Figure 13:
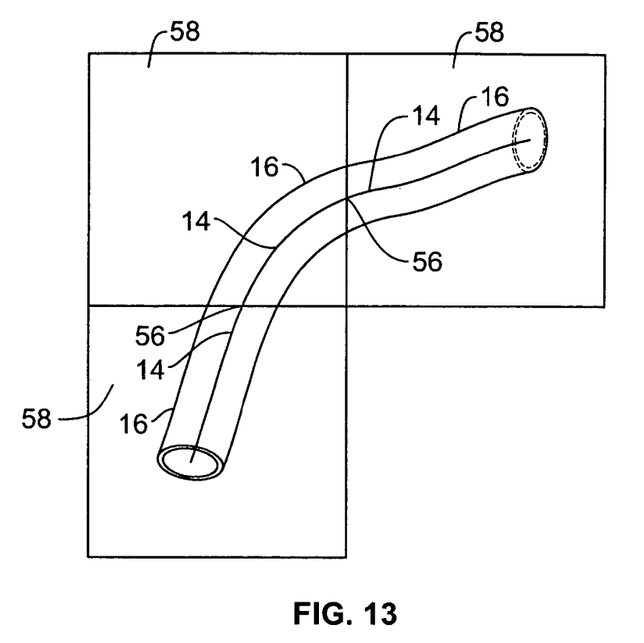
FIG. 13 is a diagrammatic view of an image of a vessel composed of multiple subsections.
Figure 14:
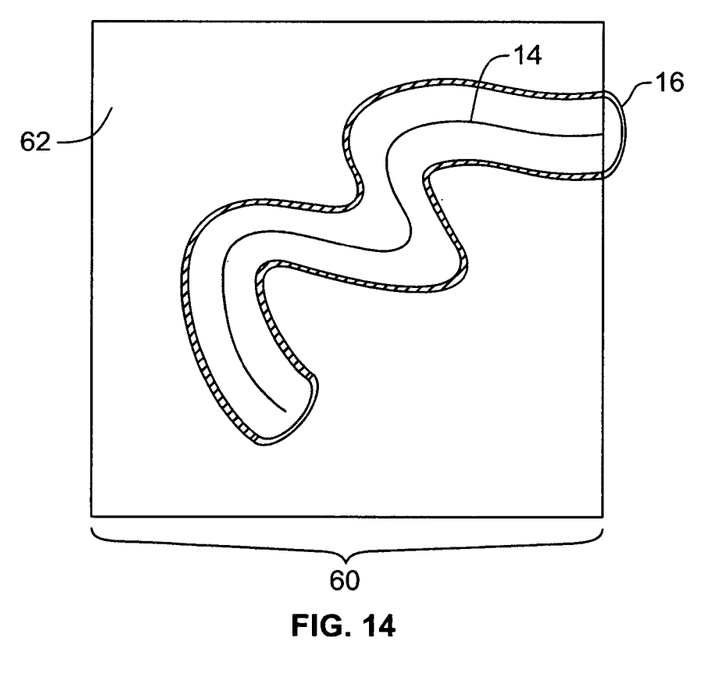
FIG. 14 is a diagrammatic view showing how a centerline can be used to bisect or divide a vessel in two.

To obtain a centerline 14 from threshold flow data, the equations listed above for obtaining the mean, median, or mode, and particularly the x and z dimensions of the mean centers of the centerline 14 would apply to values of v or p above a certain threshold value.

Figure 9:
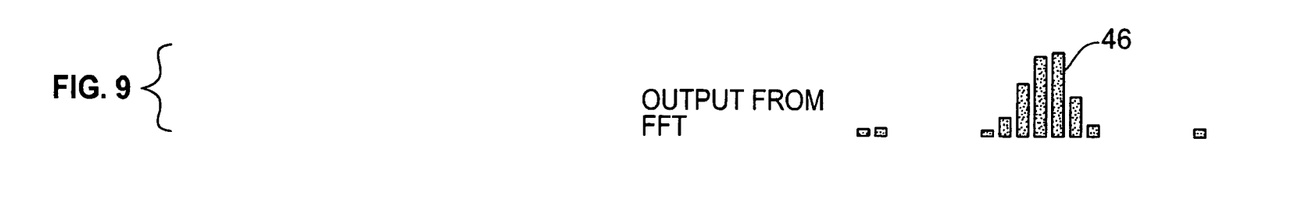
FIG. 9 is a frequency spectrum of the Doppler output power of the received signal vs. frequency after a Wall filter which intersects the FFT samples of FIG. 8.

With reference to FIG. 10, another parameter of interest is to obtain the volume of fluid 42 passing through the plane 24 per unit of time. This quantity is defined as the volume flow. Obtaining this quantity is facilitated by calculating the centerline 14 of the fluid flow. The volume flow can be obtained by at least two methods: an N-point Fast Fourier Transform (FFT) or via "4-D True Velocity Flow" color-Doppler image data.

To obtain the volume flow using an N-point FFT, reference is made now to FIGS. 8–10. The FFT samples 42 for each bin of frequencies i from an N-point FFT, where $|i|<N/2$ leads to a discrete power spectrum $p_i$, the area under the output spectrum 44 after the Wall filter, whose output appears as pseudo-bar graph elements 46. For a given voxel element n, the power spectrum in the voxel n in the frequency bin i is given by $p_{n,i}$, and the power spectrum per bin, $p_i$ is obtained by summing the per-voxel power spectrum over all voxels at a given y. The power in each frequency bin is $$p_i = \sum_n p_{n,i}; \tag{16}$$

the Doppler frequency per frequency bin is $$f_i=PRF \times i/N; \tag{17}$$

and the velocity in a frequency bin is $$v_i = \frac{c}{2f_0}f_i = \frac{PRF}{N}\frac{c}{2f_0}i; \tag{18}$$

The power-velocity integral is computed as $$F_1 = \sum_{-\frac{N}{2}-1}^{+\frac{N}{2}-1} i \times p_i \tag{19}$$

and $i \neq 0$. The volume flow is then $$\dot{Q} = kF_1/p_0 \text{ where } k = \frac{PRF}{N}\frac{c}{2f_0}\Delta x \Delta z, \tag{20}$$

where $p_0$ is the total power out of the Wall filter in a single central voxel about the centerline 14, and $\Delta x$, $\Delta z$ are the lengths of the dimensions of each voxel (n) in the summation. The result is independent of $\cos\theta$, provided that $\theta$ is not close to 90°.

Alternatively, volume flow can be estimated directly from "4-D True Velocity Flow" color-Doppler image data. Referring again to FIG. 3, the direct approach is to choose the plane 24 (the plane that cuts though the vessel 16 orthogonal to the centerline 14), sum the $s_n$'s for every non-zero pixel in the plane 24, and multiply by the pixel area. An approximate way to estimate the volume flow from raw color Doppler data is to sum the autocorrelation Doppler values over all the pixels in the vessel 16 at a fixed y, and use the slope of the centerline 14 in the y-z plane as a correction factor. The result is $$\dot{Q} = \left(\frac{c}{2f_0}\Delta x \Delta z\right)\frac{y_c}{z_c}\sum_n f_n. \qquad (21)$$

The simple $y_c/z_c$ slope simultaneously corrects for both the Doppler angle θ and the orientation angle of the x-z image plane φ without having to compute the square root of the sum of the squares that is needed to determine $s_n$.

To determine the lumen area from either power Doppler, color Doppler, or true velocity flow ($p_n$, $f_n$, or $s_n$), select the plane 24 (the plane that cuts though the vessel 16 orthogonal to the centerline 14), count the number of pixels in the vessel 16, and multiply by the pixel area. Pixels on vessel boundaries can be given a reduced weight for a more precise measurement.

Figure 15:
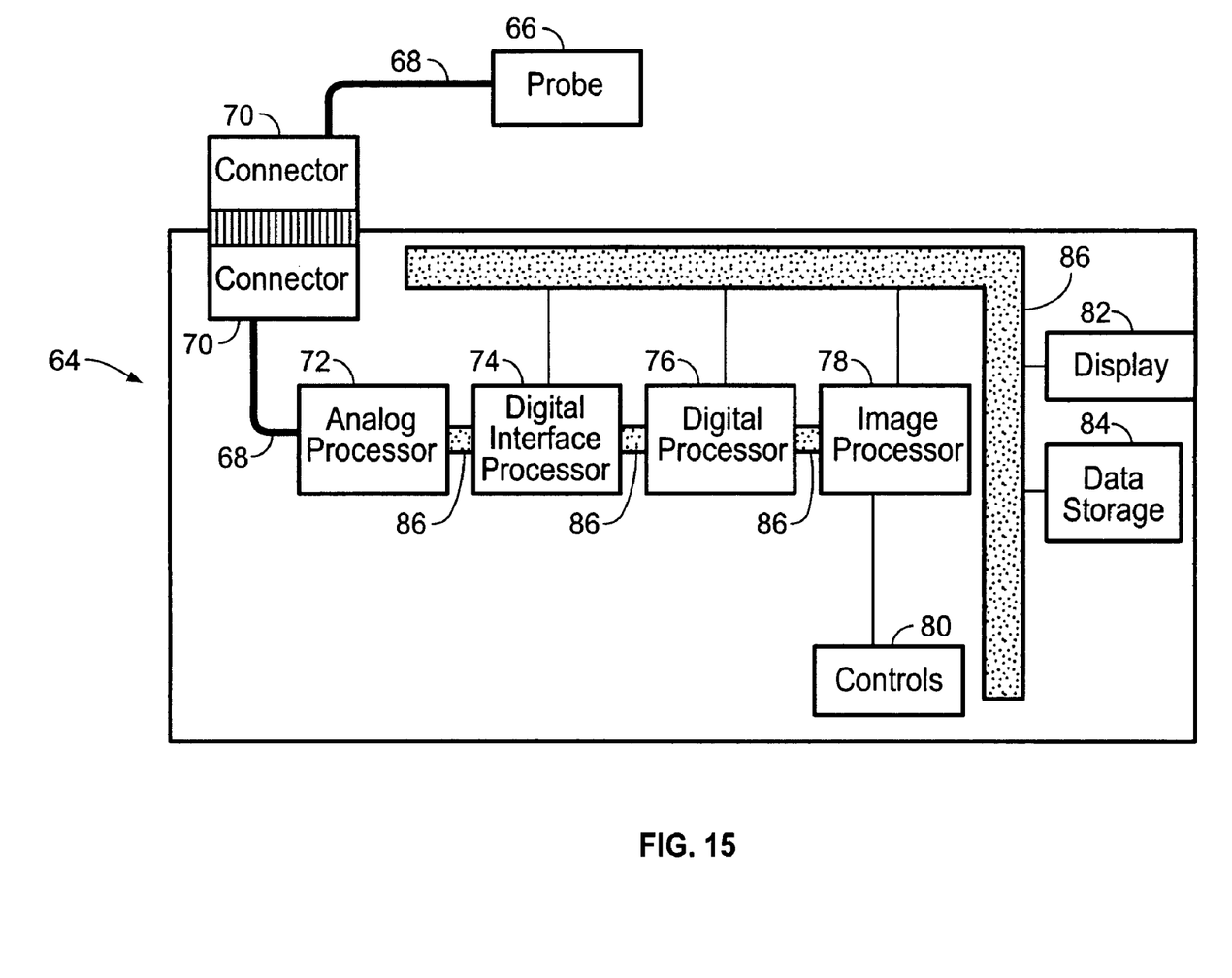
FIG. 15 depicts a block diagram of a system that implements the method in accordance with an exemplary embodiment of the present invention.

Additional parameters can be obtained or imaged once the centerline and true vector velocity is known. Referring now to FIGS. 11–14, the location of a stenosis 48 can be found as the point of highest peak true (systolic) velocity along the centerline 14 of a vessel 16. One can model the true velocity as a function of distance from the centerline to the walls 50 of the vessel 16. Since velocity is likely to be higher in the area 52 near the centerline 14 than the area 54 closer to the walls 50 of the vessel 16, a three dimensional image displaying the degree of translucency of a vessel 16 can be generated by imaging software within ultrasound equipment. That same imaging software can map the entire vessel along the entire field of view and keep track of that vessel despite the movement of a patient by beam tracking software that focuses on the location of the centerline 14. The coordinates of the endpoints 56 of several centerlines 14 can be aligned so as to "stitch" together several fields of view 58 and thus display the entire length of the vessel 16, no matter how tortuous its path. Once the centerline 14 is calculated in the field of view 60 throughout the vessel 16, a bisection 62 of the vessel 16 can be obtained from a plane 62 that slices though the centerline 14.

With reference to FIG. 15, a block diagram of a system 64 that implements the method of obtaining a centerline in accordance with an exemplary embodiment of the present invention is depicted. The system 64 includes the ultrasound probe 66, coaxial cables 68, a connector panel 70, an analog processor 72, a digital interface processor 74, a digital processor 76, an image processor 78, controls 80, a display 82, and data storage (memory) 84, interconnected as shown through a system bus 86. The ultrasound probe 66 contains a number of piezoelectric acoustic transducers (not shown) arranged as an array of elements. For 3-D or 4-D imaging, a two dimensional arrangement of elements is necessary. For 2-D imaging, a one dimensional array of 1×N elements is needed. The transducer elements can both send and receive, but the elements that transmit ultrasound pulses do not necessarily have to be the same elements of the array that receive reflections from a vessel 16. The cables 68 transmit and receive electrical impulses and are generally coaxial cables.

The analog processor 72 contains circuitry for amplification, gain management, and analog-to-digital (A/D) conversion of the ultrasound pulses to be transmitted and the received reflections from the transducer elements. Between the transmitting and receiving circuitry (not shown) is an electrical protection circuit, since the signals emanating from the transducer elements require voltages in the neighborhood of 100 V, while the received reflected signals are on the order of microvolts. Since the dynamic range of the received signal is very high, there is a need for a circuit for performing time gain control. Since reflected signals are received from different locations in the body, these signals may be out of phase with each other, so that gain for each transducer received signal is adjusted dynamically in time to line up received signals. An anti-aliasing filter is located between the receiving amplifier and the A/D converter. The A/D converter can be of a type that outputs the signal in a parallel array of bits or can output the digital data serially.

A digital interface processor (DIP) 74 receives the digital version of the received signal from the analog processor 72. The DIP 74 organizes the sampled data to put it in a proper format so that the digital processor 76 can form a beam. If the data from the A/D converter of the analog processor 72 is processed serially, then the DIP 74 can also packetize and time compress the data.

The digital processor (DP) 76 takes packetized (in the case of serial processing) or time division multiplexed (in the case of parallel processing) data and forms a beam representing the array of transduced elements in the ultrasound probe. 66. For each transduced element, a time delay is added to cause all elements of the combined wavefront to be in phase. After beam forming, the combined beam contains the wavefronts represented by the frequency shifted Doppler signal. At this point, the Doppler information is separated from the non-Doppler information using a Wall filter as previously discussed with reference to FIGS. 7–9. The imaginary part, I, and the real part, Q, from the autocorrelation functions of the data as previously discussed are extracted. The Doppler information is separated from the non-Doppler information by taking the arctangent of I/Q from which the angle is proportional to the radial component of the true velocity of the blood flow. The image processor 78 takes this output, organizes the data into volumes and generates the centerline 14, and from the centerline 14 the true vector velocity, blood volume flow, lumen area, and other parameters of interest. The image processor 78 then puts these parameters in a format for displaying on the display 82. The controls hardware/software 80 provides the man-machine interface to a user, so that a user can use an input device such as a joy stick to highlight portions of the centerline and display measurements. The data storage 84, which can include RAM, ROM, floppy disks, hard disks, and/or optical media, provides the memory necessary for the DIP 74, the digital processor 76, and the image processor 78 to carry out their specific functions.

It will be understood that the embodiments described herein are merely exemplary and that a person skilled in the art may make many variations and modifications without departing from the spirit and scope of the invention. All such variations and modifications are intended to be included within the scope of the invention.

What is claimed is:

1. A method for determining the location of an effective center of a fluid flow in a vessel, comprising the steps of:
    (A) propagating ultrasound energy along an axis of propagation Z in a spacial coordinate system (x, y, z) in which the dimension z is in the same direction as the axis of propagation Z;
    (B) projecting the ultrasound energy upon the vessel defining a set of coordinates in the spacial coordinate system where the ultrasound energy impinges upon fluid in the vessel at a given value of the dimension y;
    (C) receiving a Doppler-shifted signal reflected from the fluid in the vessel at a plurality of said set of coordinates,
    (D) deriving a set of quantities expressed as a density from the Doppler-shifted signal for each of said set of coordinates, the density being a function of the Doppler shift in frequency associated with each of said set of coordinates, the density being indicative of the movement of the fluid; and (E) calculating one of the mean, mode or median of each of the dimensions of said set of coordinates in conjunction with the density associated therewith.

2. The method of claim 1, wherein said set of coordinates approximates at least a portion of a conic section.

3. The method of claim 1, further comprising the steps of repeating said steps (A)–(E) after changing the set of coordinates to a second set of coordinates to determine another center in the fluid flow at a different point along the length of the vessel and then determining a vector v which connects the two centers and indicates the approximate direction of flow and the approximate centerline.

4. The method of claim 3, further comprising the step of repeating said steps (A)–(E) for a plurality of center points and vectors to ascertain a centerline of the vessel over an entire field of view.

5. The method of claim 4, wherein said density is derived from at least one of Power Doppler measurements, Color Doppler measurements, and threshold flow data.

6. The method of claim 5, wherein said Power Doppler measurements occur after a Wall filter.

7. The method of claim 5, wherein said Color Doppler measurements are derived from the radial component of true velocity flow in the direction of the dimension z.

8. The method of claim 5, wherein said at least one of Power Doppler measurements, Color Doppler measurements, and threshold flow data is based on at least one of 2-D, 3-D and 4-D ultrasound techniques.

9. The method of claim 3, further comprising the step of dividing said set of coordinates into a plurality of voxels before said step (E).

10. The method of claim 9, wherein the mean is calculated as a sum of the value of the density in a voxel multiplied by the value of one of the dimensions other than z of said voxel divided by the sum of the value of densities associated with the plurality of voxels.

11. The method of claim 3, wherein the step of determining the vector v includes finding the difference between the corresponding dimensions of the effective center and the another center.

12. The method of claim 11, wherein the special coordinate system is a rectangular coordinate system and wherein said step of determining the vector v is calculated in accordance with the following mathematical statement of proportionality:

$$v=(v_x, v_y, v_z) \propto (\bar{x}(y_2)-\bar{x}(y_1), y_2-y_1, \bar{z}(y_2)-\bar{z}(y_1)).$$

13. The method of claim 11, wherein the speed s of the vector v is calculated by dividing the measured radial velocity by the cosine of the angle between the z direction and the direction of the approximate centerline.

14. The method of claim 13, wherein the radial component $v_n$ of the vector $v_n$ in a voxel n is related to the measured Doppler frequency $$f_n \text{ by } v_n = \frac{c}{2f_0} f_n,$$

where c is the sonic propagation speed and $f_0$ is the sonic propagation frequency, and further comprising the step of determining the speed $s_n$ in the voxel n in accordance with the formula $$s_n(x, y, z) = \frac{c}{2f_0} \frac{\sqrt{(x-a)^2+(y-b)^2+z^2}}{(x-a)v_x+(y-b)v_y+zv_z} f_n(x, y, z)$$

where the coordinate (a, b, 0) is located at the center of a sub-array of said ultrasound probe currently active to observe the point (x, y, z), where the Doppler frequency $f_n$=(PRF/2$\pi$) a $\tan_2$[Im(F)/Re(F)], where Im(F) is the imaginary part of the quantity F and Re(F) is the real part of the quantity F, where PRF is the ultrasound pulse repetition frequency, where the quantity F is the autocorrelation function of the complex wall filter output at a lag of one.

15. The method of claim 13, wherein the radial component $v_n$ of the vector $v_n$ in a voxel n is related to the measured Doppler frequency $$f_n \text{ by } v_n = \frac{c}{2f_0} f_n,$$

where c is the sonic propagation speed and $f_0$ is the sonic propagation frequency, and further comprising the step of determining the speed $s_n$ in the voxel n in accordance with the formula $$s_n = \frac{cf_n}{2f_0} \frac{\sqrt{x_c^2+y_c^2+z_c^2}}{z_c}$$

where $x_c$, $y_c$, $z_c$ are the coordinates of a point on the centerline relative to another point on the centerline (0, 0, 0), both points being in the vicinity of where $f_n$ is measured.

16. The method of claim 15, wherein volume flow, $\dot{Q}$, is related to the Doppler frequency, $f_n$, by the formula $$\dot{Q} = \left(\frac{c}{2f_0} \Delta x \Delta z\right) \frac{y_c}{z_c} \sum_n f_n$$

where $\Delta x$, $\Delta z$ are the lengths of the dimensions of each voxel (n) in the summation.

17. The method of claim 15, wherein volume flow, $\dot{Q}$, is related to the Doppler frequency, $f_n$, by the formula $\dot{Q}=kF_1/p_0$ where $$k = \frac{PRF}{N} \frac{c}{2f_0} \Delta x \Delta z, \quad F_1 = \sum_{-\frac{N}{2}-1}^{+\frac{N}{2}-1} i \times p_i, i \neq 0, \quad p_i = \sum_n p_{n,i},$$

where $\Delta x, \Delta z$ are the lengths of the dimensions of each voxel (n) in the summation, where $p_0$ is the total power output of the Wall filter for a central voxel running through the centerline, where the value N is the number of points used to calculate an N-point Fast Fourier Transform of the discrete power spectrum $p_{n,i}$ coming out of said Wall filter, and where i is the $i^{th}$ bin of said discrete power spectrum $p_{n,i}$.

18. The method of claim 9, further comprising the step of determining the lumen area by
  (F) selecting a plane perpendicular to the centerline;
  (G) finding the intersection of the plane with the vessel; and
  (H) counting the number of pixels within the intersection.

19. The method of claim 15, further including the step of displaying a color on a display corresponding to the vector $v_n$ of a voxel n.

20. The method of claim 15, further including the step of displaying the degree of translucency in a vessel on a display based on the vector $v_n$ of a voxel n.

21. The method of claim 15, further including the steps of:
  (F) obtaining the vector $v_n$ in at least one voxel running through the centerline calculated at a first point in time; and
  (G) adjusting a beam associated with an ultrasound probe to relocate the vector $v_n$ found in said step (F).

22. The method of claim 15, further including the steps of:
  (F) obtaining a plurality of true vector velocities for a plurality of voxels running through the centerline; and
  (G) finding the peak systolic velocity from the plurality of true vector velocities.

23. The method of claim 15, further including the step of finding the peak speed of the true vector velocity from a plurality of true vector velocities on the centerline to locate the position of a stenosis in said vessel.

24. The method of claim 15, wherein the centerline has a first set of coordinates corresponding to the intersection of the centerline with one edge of the field of view, said method further comprising the steps of:
  (F) repeating said steps (A)–(E) for a plurality of center points and vectors to ascertain a first centerline of the vessel over a first field of view;
  (G) repeating said steps (A)–(E) for a plurality of center points and vectors to ascertain a second centerline of the vessel over a second field of view; and
  (H) aligning the first centerline with the second centerline to form a composite image of the first and second fields of view.

25. The method of claim 15, further including the steps of:
  (F) modeling the vessel on a display based on finding the true vector velocity over a plurality of voxels and the centerline;
  (G) slicing the vessel into at least two sections via a plane that passes through the walls of the vessel and the centerline; and
  (H) displaying one of the at least two sections of the vessel on a display.

26. An ultrasound apparatus comprising:
a transducer array for:
  (A) propagating ultrasound energy along an axis of propagation Z in a spacial coordinate system (x, y, z) in which the dimension z is in the same direction as the axis of propagation Z;
  (B) projecting the ultrasound energy upon the vessel defining a set of coordinates in the spacial coordinate system where the ultrasound energy impinges upon fluid in the vessel at a given value of the dimension y;
  (C) receiving a Doppler-shifted signal reflected from the fluid in the vessel at a plurality of said set of coordinates; and
a processor for:
  (D) deriving a set of quantities expressed as a density from the Doppler- shifted signal for each of said set of coordinates, the density being a function of the Doppler shift in frequency associated with each of said set of coordinates, the density being indicative of the movement of the fluid; and
  (E) calculating one of the mean, mode or median of each of the dimensions of said set of coordinates in conjunction with the density associated therewith.

27. The apparatus of claim 26, wherein said set of coordinates approximates at least a portion of a conic section.

28. The apparatus of claim 27, wherein said processor performs said functions (A)–(F) after changing the set of coordinates to a second set of coordinates to determine another center in the fluid flow at a different point along the length of the vessel and then determining a vector v which connects the two centers and indicates the approximate direction of flow and the approximate centerline.

29. The apparatus of claim 28, wherein said processor performs said functions (A)–(E) for a plurality of center points and vectors to ascertain a centerline of the vessel over an entire field of view.

\* \* \* \* \*